United States Patent [19]

Yoshioka

[11] Patent Number: 5,090,413
[45] Date of Patent: Feb. 25, 1992

[54] ULTRASONIC DIAGNOSTIC APPARATUS

[75] Inventor: Yoshihisa Yoshioka, Tochigi, Japan

[73] Assignee: Kabushiki Kaisha Toshiba, Kawasaki, Japan

[21] Appl. No.: 571,161

[22] Filed: Aug. 23, 1990

[30] Foreign Application Priority Data

Aug. 29, 1989 [JP] Japan ................................. 1-222677

[51] Int. Cl.$^5$ ............................................... A61B 8/00
[52] U.S. Cl. ............................ 128/660.07; 128/660.05
[58] Field of Search ...................... 128/660.07, 660.05, 128/660.04, 660.01, 661.07

[56] References Cited

U.S. PATENT DOCUMENTS

| 4,413,630 | 11/1983 | Anderson et al. | 128/660.07 |
| 4,719,509 | 1/1988 | Sakamoto | 128/660.07 |
| 4,848,354 | 7/1989 | Angelsen et al. | 128/660.05 |
| 4,924,869 | 5/1990 | Takeuchi et al. | 128/660.05 |
| 4,932,414 | 6/1990 | Coleman et al. | 128/660.07 |

FOREIGN PATENT DOCUMENTS

| 0079453A1 | 5/1983 | European Pat. Off. | 128/660.05 |
| 0157302A1 | 10/1985 | European Pat. Off. | 128/660.07 |
| 0190979A3 | 8/1986 | European Pat. Off. | 128/661.08 |

Primary Examiner—Francis Jaworski
Assistant Examiner—George Manuel
Attorney, Agent, or Firm—Finnegan, Henderson, Farabow, Garrett and Dunner

[57] ABSTRACT

In the ultrasonic diagnostic apparatus arranged to simultaneously display two diagnostic images in the left and right halves on one display screen, there is provided a bulk storage such as an optical disk wherein the images from an ultrasonic diagnostic imaging device are stored. The images from the ultrasonic diagnostic imaging device, and those from the bulk storage are supplied to first and/or second frame memories. In the recording mode of the bulk storage, the images from the ultrasonic diagnostic imaging device are written into the bulk storage and also into the first and/or second frame memories, the former being for displaying a frozen still picture and the latter being for displaying a motion picture. In the playback mode of the bulk storage, the playback images from the bulk storage are written into only the first frame memory or the second frame memory. The playback images are displayed as a motion picture and a still image frozen at the time of recording is displayed.

14 Claims, 4 Drawing Sheets

| MODE | FRAME MEMORY | | SELECTOR | |
|---|---|---|---|---|
| | 24 | 26 | 16 | 20 |
| PLAYBACK | FREEZE | MOTION PICTURE | OFF | 20b |
| DUAL | MOTION PICTURE | FREEZE | 16b | OFF |
| FREEZE & PLAYBACK | FREEZE | MOTION PICTURE | OFF | 20b |
| | | FREEZE | | OFF |
| LIVE & PLAYBACK | LIVE | PLAYBACK | 16a | 20b |
| | FREEZE | FREEZE | OFF | OFF |

FIG. 4

ULTRASONIC DIAGNOSTIC APPARATUS

BACKGROUND OF THE INVENTION

1. Field of the Invention

The present invention relates to an ultrasonic diagnostic apparatus, and more particularly to an ultrasonic diagnostic apparatus having a display screen which is segmented into several areas so as to simultaneously display several ultrasonic diagnostic images.

2. Description of the Related Art

There is a conventional ultrasonic diagnostic apparatus with a so-called dual display function. The conventional apparatus includes two frame memories for the display of two ultrasonic diagnostic images; each of these frame memories corresponding to one of the two segments into which the display screen is divided. In this apparatus, for example, B-mode ultrasonic images are sequentially written into a first frame memory, the image being written into the first frame memory is frozen at a given timing, and the B-mode images are written into a second frame memory after the given timing. Therefore, a still picture (frozen image) and a motion picture (live image) are displayed on the screen side by side. In other words, in the conventional dual display ultrasonic diagnostic apparatus, input images are frozen and displayed as a still picture by using the first frame memory and input images are displayed as a motion picture (live image) on a real time basis by using the second frame memory.

On the other hand, with the recent increase in the recording density of data recording medium, it is possible for a large number of diagnostic images for each patient to be recorded. Therefore, the diagnostic images which are displayed on the display screen are written into bulk storage, such as an optical disk device, at the time of diagnosis. The input signal to the display is branched to the bulk storage and written therein in the recording mode. Thus, the images can be recorded without any effect upon the images currently displayed on the dual-display screen.

In the playback mode, the input signal to the display is changed from the one used in the recording mode, that is, the playback image signal is supplied to the display (frame memory) instead of the live image signal from the ultrasonic diagnostic imaging circuit. Since the type of the signal input to the display changes when the mode of the bulk storage changes to the playback mode, the playback signal is supplied to the display after clearing the contents of the respective frame memories.

Therefore, the playback images are frozen and displayed as a still picture by using the first frame memory and the playback images are displayed as a motion picture by using the second frame memory. However, it is not possible to display an image frozen at the time of recording as a still picture and playback images as a motion picture. Namely, the conventional ultrasonic diagnostic apparatus may only be operated in a dual display mode wherein a live picture signal is displayed as a still picture (frozen image) and a motion picture is displayed on another dual display mode wherein a playback signal from the bulk storage is displayed as a still picture is displayed and a motion picture. The prior apparatus is not able to be operated with a dual display mode wherein a live picture signal is displayed as a still picture and a playback signal is displayed as a motion picture, giving rise to inconvenience during diagnosis.

SUMMARY OF THE INVENTION

It is an object of the present invention to provide an ultrasonic diagnostic apparatus having bulk storage for storing images and which is operated with a dual display mode wherein a live ultrasonic diagnostic image and a playback image read out from the bulk storage are displayed side by side as a motion picture and/or a still picture in accordance with the need of a user.

The ultrasonic diagnostic apparatus according to the present invention comprises imaging means for transmitting an ultrasonic beam to a subject, receiving the ultrasonic beam reflected by the subject, and providing an image representing ultrasonic reflection characteristic of the subject according to the ultrasonic beam received, display means for displaying the image provided by the imaging means and comprising a first frame memory and a second frame memory whose outputs are displayed side by side and both of which can freeze the image, storage means connected to the imaging means for storing a plurality of images, and recording/playback control means, connected to the imaging means, storage means, and display means, for writing, in the recording mode, the image provided by the imaging means into the first and second frame memories and storage means, and for writing, in the playback mode, the image output from the storage means into one of the first and second frame memories and for inhibiting writing into the other of the first and second frame memories.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 4 is a diagram explaining the operation of the embodiment in the playback mode.

DETAILED DESCRIPTION OF THE PREFERRED EMBODIMENTS

Figure 1:
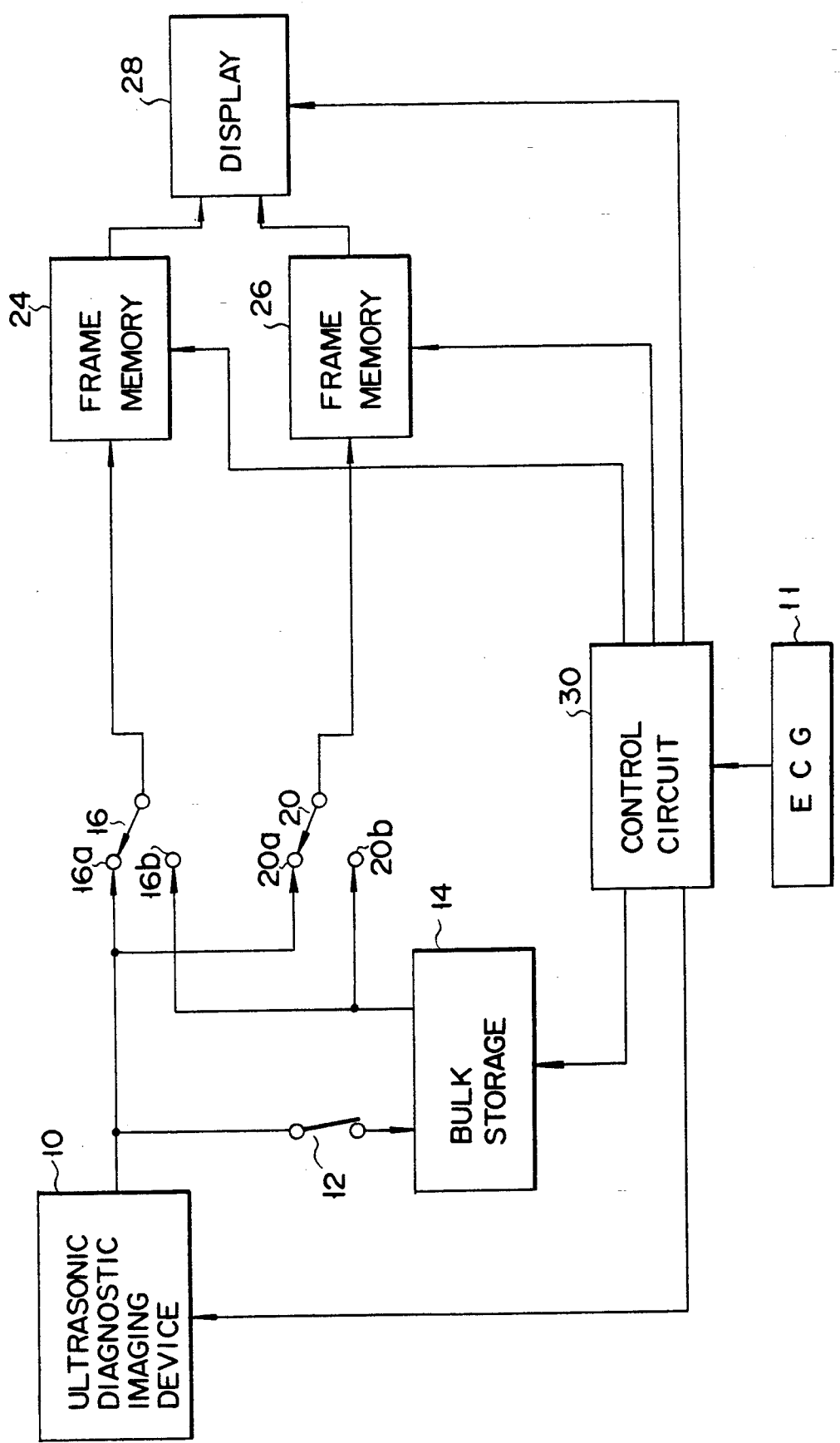
FIG. 1 is a block diagram showing an ultrasonic diagnostic apparatus according to an embodiment of the present invention.

A preferred embodiment of an ultrasonic diagnostic apparatus according to the present invention will now be described with reference to the accompanying drawings. FIG. 1 is a block diagram showing the embodiment. An image signal from an ultrasonic diagnostic imaging device 10 is supplied via a recording switch 12 to bulk storage 14 comprising an optical disk device or the like and is also supplied through first terminals 16a and 20a of selectors 16 and 20 to frame memories 24 and 26, respectively. The output terminal of the ultrasonic diagnostic imaging device 10 is commonly connected to first terminals 16a and 20a of the selectors 16 and 20. Second terminals 16b and 20b of the selectors 16 and 20 are commonly connected to the output terminal of the bulk storage 14.

Figure 2:
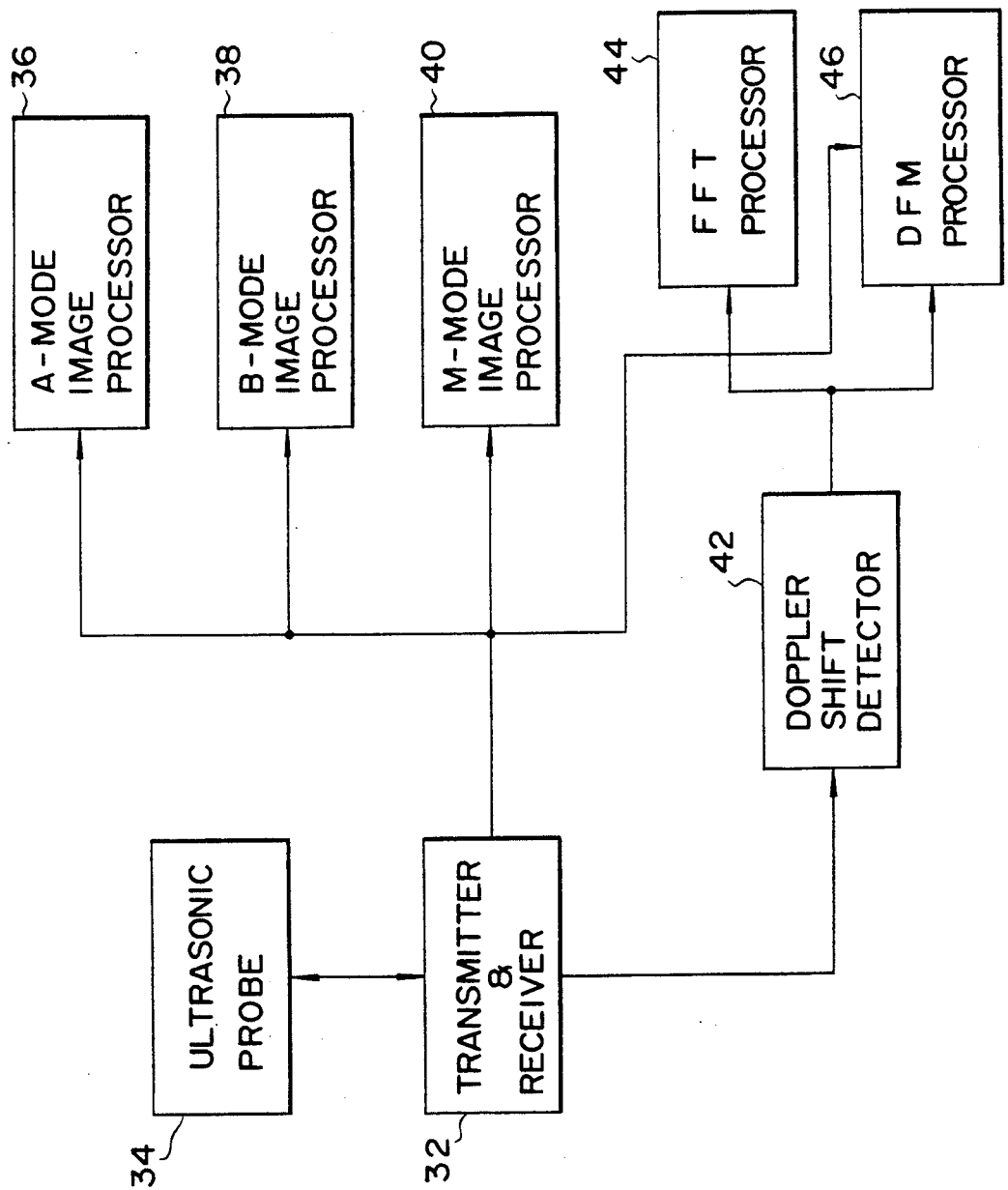
FIG. 2 is a block diagram showing details of an ultrasonic diagnostic imaging device included in the embodiment.

The ultrasonic diagnostic imaging device 10 may comprise known circuitry; for example, it may be configured as shown in FIG. 2. A transmitter & receiver 32 is connected to an ultrasonic probe 34. The ultrasonic probe 34 of an electronic sector scanning type comprises a plurality of ultrasonic transducers aligned in a line. The ultrasonic beams can be scanned in a sector manner or focused by changing the timing of application of the voltage to these individual transducers. The ultrasonic probe 34 is not limited to the electronic sector scanning type but may be of an electronic linear scanning type or a mechanical scanning type. The transmitter & receiver 32 comprises a scanning circuit (including a delay circuit) to scan the ultrasonic beams, a reference oscillator to determine the frequency of ultrasonic oscillation of the transducers, a transmission unit including a pulse generator to determine the ultrasonic beam radiation repetitive frequency (rate frequency), a preamplifier to process the signal received by the probe 34, an adder, and a reception unit including a detector, and so forth. The detector detects the intensity of the echo wave of the ultrasonic beam in each ultrasonic beam radiation direction (raster direction).

The output of the detector is coupled to an A-mode image processor 36, a B-mode image processor 38, and an M-mode image processor 40. The A-mode image processor 36 generates an image signal representing a time-variation in the intensity of the echo ultrasonic wave in a given raster direction. The B-mode image processor 38 converts the intensity of the ultrasonic echo wave in each raster direction to the luminance signal which is subsequently applied for two-dimensional signal processing whereby an image signal representing a sectional image is generated. The M-mode image processor 40 moves the time axis of the A-mode image at a given rate in the direction orthogonal to the raster direction thereby to generate a waveform signal representing the movements of an object at which the ultrasonic wave is reflected.

The signal input to the detector in the transmitter & receiver 32 and the output signal of the reference oscillator in the transmitter & receiver 32 are supplied to a Doppler shift detector 42. The Doppler shift detector 42 detects a Doppler shift frequency by means of the orthogonal detection system and comprises two mixers, two 90° phase shifters, two low-pass filters, and so on. The output of the Doppler shift detector 42 is supplied to an FFT (Fast Fourier Transform) processor 44 for spectrum analysis of a received signal, and also to a DFM (Doppler Flow Mapping) processor 46. The DFM processor 46 generates an image signal representing a flow rate of blood as a chromatic image, the flow rate being chromatically mapped on the B-mode or M-mode image. One or more of the image signals obtained from the A-mode image processor 36, B-mode image processor 38, M-mode image processor 40, FFT processor 44, and DFM processor 46 are selectively output from the ultrasonic diagnostic imaging device 10. These processors are of known types, and no more detailed description will be presented here.

Referring back to FIG. 1, the output from the bulk storage 14 is supplied to the frame memories 24 and 26 through the second terminals 16b and 20b of the selectors 16 and 20. The selectors 16 and 20 are used for freezing the image. By turning off each of these selectors 16 and 20, each of the images being written into the frame memories 24 and 26 is frozen. The selectors 16 and 20 are also used for selecting one of the output signals from the ultrasonic diagnostic imaging device 10 or the bulk storage 14 to selectively supply the desired output to the frame memories 24 or 26. The outputs from the frame memories 24 and 26 are supplied to a display 28 wherein they are displayed side by side, respectively in the left and right halves of the display screen.

The control signal from a control circuit 30 for controlling the entire system of the ultrasonic diagnostic apparatus is supplied to the ultrasonic diagnostic imaging device 10, recording switch 12, bulk storage 14, selectors 16 and 20, frame memories 24 and 26, and display 28. The output of an electrocardiograph 11 for detecting movement of a patient is supplied to the control circuit 30 whereby it is possible to synchronize the recording of an ultrasonic image output from the ultrasonic diagnostic imaging device 10 into the bulk storage 14 and the playback of each recorded ultrasonic image signal from the bulk storage 14 with the phase of the heart beat.

Figure 3:
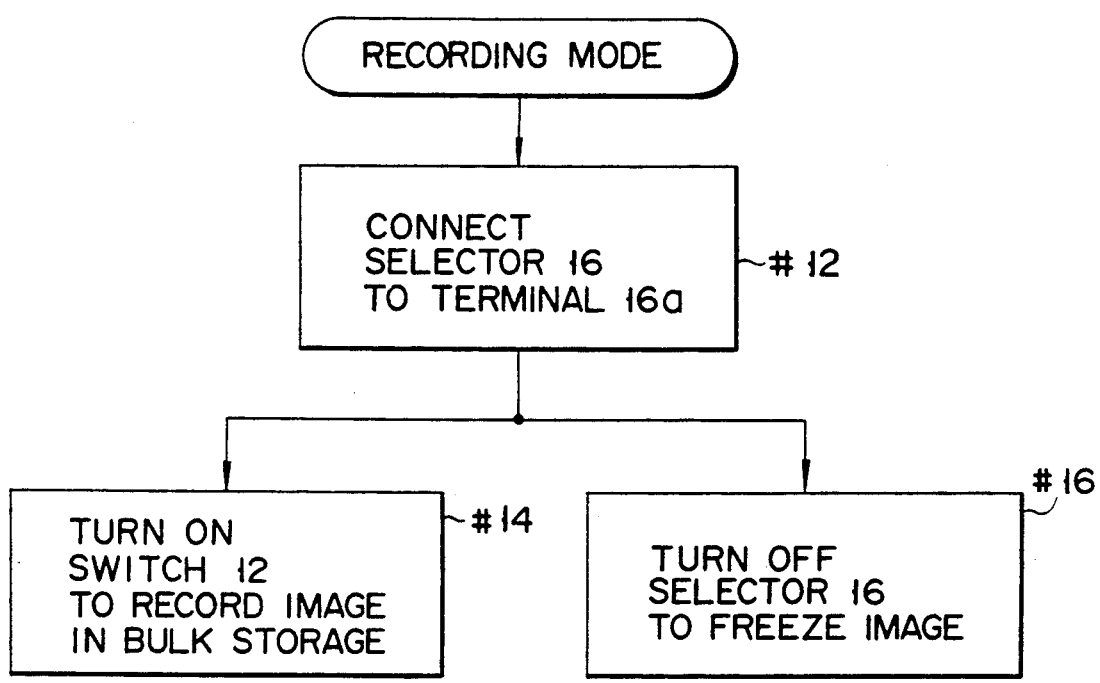
FIG. 3 is a flowchart representing the operation of the embodiment in the recording mode.

The operation of the embodiment will now be described. This embodiment includes two operation modes; one is a recording mode and the other is a playback mode. FIG. 3 is a flowchart illustrating the operation in the recording mode. In step #12, the selector 16 is connected to the first terminal 16a to supply the live image signal from the ultrasonic diagnostic imaging device 10 to the frame memory 24. As a result, either the B-mode image or the M-mode image signals is sequentially written into the frame memory 24 through the selector 16 and subsequently displayed as a motion picture in the left half of the screen of the display 28.

In step #14, following the acquisition of a desired image, the recording switch 12 turns on to record the ultrasonic diagnostic image currently displayed on the display 28 into the bulk storage 14.

In step #16, following the acquisition of a desired image, the selector 16 is turned off (is is disconnected from both of the first and second terminals) in order to freeze the image signal being written into the frame memory 24. This frozen image is displayed in the left half of the display screen as a still picture. Thereafter, the selector 20 is connected to the first terminal 20a to write the live image signal from the imaging device 10 into the frame memory 26. A motion picture is displayed in the right half of the display 28 based on the output signal from the imaging device 10.

In the above description, dual display is performed with a still picture and a motion picture which are both B-mode images. However, one of these pictures may be another mode image. Namely, it is possible to freeze an M-mode image and to display a live B-mode image as a motion picture corresponding to the slice of the patient at which the M-mode image is frozen. In this instance, the former dual display is called a "B dual mode" and the latter is called an "(M +B)" mode.

As in the foregoing, by merely turning on the recording switch 12, the image signal which is currently displayed on the display 28 can be recorded into the bulk storage 14 without effecting the image displayed. In addition, since the display 28 has a dual display function, it can display side by side a live image from the ultrasonic diagnostic imaging device 10 as a motion picture and a still picture prepared by freezing the live image at a desired time.

Next, the operation in the playback mode is described. Here, the recording switch 12 is turned off. The playback mode includes three cases. A description will be made of the first case where dual display is performed with two dual playback images. In this playback mode, one of the selectors 16 and 20 is connected to the second terminals 16b and 20b. The other of the selectors 16 and 20 is turned off. Therefore, the playback signals from the bulk storage 14 are supplied to one of the frame memories 24 and 26 through one of the selector 16 and 20 and then they are displayed in the display 28 as a motion picture. Likewise in the recording mode, the appropriate selector 16 or 20 is turned off when the image is to be frozen. After freezing the image, the other selector which has been turned off is connected to the second terminal. Further, it is noted that dual display in the playback mode can be performed with the M-mode playback image as a frozen image and the B-mode playback image corresponding to the slice at which the M-mode image is frozen as a motion picture.

Next, the operation in the second case where the playback image signal is displayed either as a motion picture or a still picture and a still image obtained by freezing the live image at the time of recording is kept displayed on the display screen will be described. In this dual freeze and playback mode, the selector 16 is turned off and the selector 20 is connected to the second terminal 20b. With these connections, playback signal writing into the frame memory 24 which holds the frozen image is inhibited, therefore retaining the frozen image therein. Thus, ultrasonic image data is not written into the frame memory 24 but the playback image signal from the bulk storage 14 is written into the frame memory 26 through the selector 20, whereby the dual display is performed with a frozen picture stored in the frame memory 24 in the recording mode and the playback image written into the frame memory 26. Under this condition, the playback image is displayed as a motion picture. In order to freeze the playback image, it suffices to turn off the selector 20. Also in this case, it is possible to perform the dual display with different types of images, e.g., the M-mode image and the corresponding B-mode image.

Finally, a description will now be made of the third case where a live image from the ultrasonic diagnostic imaging device 10 and a playback image from the bulk storage 14 are displayed simultaneously with the former in the left half and the latter in the right half of the display screen. In this case, the selector 16 is connected to the first terminal 16a and the selector 20 is connected to the second terminal 20b. Thus, a live image from the ultrasonic diagnostic imaging device 10 is written into the frame memory 24 through the selector 16 while a playback image signal from the bulk storage 14 is written into the frame memory 26 through the selector 20. Under this condition, both the live image and the playback image are displayed as motion pictures To freeze these motion pictures, it suffices to turn off the selectors 16 and 20, and subsequently inhibit the writing of the ultrasonic image into the frame memories 24 and 26. Also in this case, dual display may be performed with different types of images, e.g., the M-mode image and the corresponding B-mode image. FIG. 4 shows the status of the frame memories 24 and 26 in the above-quoted three different cases in the playback mode, and the connection states of the selectors 16 and 20.

With the preferred embodiment of the present invention, use of the dual display in the second case in the playback mode (freeze & playback mode) and the third case (live & playback mode) enables the following advantageous diagnostic procedure.

In one of the diagnoses, one category of dual B-mode image display is utilized wherein the B-mode images obtained while a subject is quiet are stored in the bulk storage 14. Thereafter, B-mode images are obtained while the subject is applied with a movement load and they are displayed as a motion picture using the frame memory 24. It is possible to freeze the live image in the frame memory 24 when a desired image is acquired. The operation mode of the bulk storage 14 is changed to the playback mode, and the playback images therefrom are written into the frame memory 26 through the selector 20, to display the playback image as a motion picture. The result is that the playback image obtained when the patient is quiet and the live image obtained while the patient is applied with the movement load are displayed side by side, thus rendering ease of diagnosis through a comparison.

In another diagnostic, one category of (M+B) mode is utilized wherein the B-mode images are stored into the bulk storage 14. The M-mode live image is displayed, and subsequently, at a desired time, the M-mode image is frozen in the frame memory 24. The B-mode images corresponding to the time phase included in the time axis of the M-mode image frozen in the frame memory 26 are read out from the bulk storage 14, whereby the M-mode freeze image and the B-mode images (playback images) are displayed side by side. Thus, it becomes feasible to measure both the B-mode and M-mode images at their optimal time phases, resulting in increased the efficiency of diagnosis. It is noted that an M-mode image from the DFM (Doppler Flow Mapping) processor or a waveform image representing a spectrum-analyzed (FFT) wave may be used as the above M-mode image including the time-variation information.

As in the foregoing, the preferred embodiment of the present invention enables a dual display with an image frozen in the recording mode and the playback image side by side, with ease of various comparative diagnosis. Further, with the preferred embodiment of this invention, when the operation mode of the bulk storage is changed from the recording mode to the playback mode, it is not required to reset the frame memories, thus resulting in decreasing the time up to the start of playback image display.

The present invention is not limited to the aforementioned preferred embodiment but may have modifications with regard to a live-playback image dual display mode. As described above, according to the present invention, an ultrasonic diagnostic apparatus is provided capable of displaying a plurality of images at least in two parts of the display screen, writing the diagnostic image into a bulk storage while displaying the image on the display screen in the recording mode, and in the playback mode, displaying a plurality of playback and live images in optimal combinations, thereby increasing the diagnosis efficiency.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An image displaying method for an ultrasonic diagnostic apparatus wherein an ultrasonic wave is transmitted to a subject, an ultrasonic echo reflected from the subject is received, and a diagnostic image of the subject is generated according to the received ultrasonic echo, said method comprising the steps of:

storing a first diagnostic image generated while the subject is in a resting state into a bulk storage;

displaying as a motion picture a second diagnostic image generated in response to a subject a movement load;

freezing the displayed second diagnostic image at a desired time; and displaying the first diagnostic image from said bulk storage as a motion picture simultaneously with the display of the frozen second diagnostic image.

2. The method according to claim 1, wherein said first and second diagnostic images each includes a B-mode image of a cross section of a desired part of the subject.

3. An image displaying method for an ultrasonic diagnostic apparatus wherein an ultrasonic wave is transmitted to a subject, an ultrasonic echo reflected from the subject is received, and a diagnostic image of the subject is generated according to the received ultrasonic echo, said method comprising the steps of:

storing a first B-mode image of a cross section of a desired part of the subject into a bulk storage;

displaying a second diagnostic image showing a time-variation in response to a movement of the subject during a desired time period;

freezing the second displayed diagnostic image at a desired time;

reading out from said bulk storage the first B-mode image corresponding to the time period of said frozen second diagnostic image; and displaying the first B-mode image read out from said bulk storage as a motion picture simultaneously with the display of the frozen second diagnostic image.

4. The method according to claim 3, wherein said second diagnostic image includes an M-mode image representing the movement of an ultrasonic wave reflective object of the subject and a spectrum analysis waveform representing the time-variation of a Doppler shift frequency of the received ultrasonic echo.

5. An ultrasonic diagnostic apparatus comprising:

imaging means for transmitting an ultrasonic wave to a subject, receiving an ultrasonic echo reflected from the subject, and producing an image showing the ultrasonic wave reflective characteristic of the subject according to the received ultrasonic echo;

display means, including first and second frame memory means for storing a first image and a second image, respectively, output from said imaging means, for displaying the first and second images stored in the first and second frame memory means, the first and second images being displayed side by side, the display means further including means for freezing the first and second images stored in the first and second memory means;

image storage means connected to said imaging means for storing a plurality of images; and recording/playback control means connected to said image storage means and said display means for storing, in a recording mode, the image from said imaging means into the first and second frame memory means and also into said image storage means, for storing, in a playback mode, the output from said image storage means into one of the first and second frame memory means, and for prohibiting the storing of said output into the other of the first and second frame memory means.

6. The ultrasonic diagnostic apparatus according to claim 5, wherein said imaging means outputs an A-mode image, and wherein said recording/playback means reproduces a frozen A-mode image.

7. The ultrasonic diagnostic apparatus according to claim 5, wherein said imaging means outputs a B-mode image and an M-mode image, said display means freezes the M-mode image at a given time period, and said recording/playback means reproduces the B-mode image corresponding to said time period.

8. The ultrasonic diagnostic apparatus according to claim 5, wherein said imaging means outputs a B-mode image, and wherein said recording/playback control means reproduces a frozen B-mode image.

9. The ultrasonic diagnostic apparatus according to claim 5, wherein said imaging means outputs an M-mode image, and wherein said recording/playback means reproduces a frozen M-mode image.

10. The ultrasonic diagnostic apparatus according to claim 5, wherein said imaging means outputs a spectrum analysis waveform of a Doppler shift frequency, and wherein said recording/playback control means reproduces a frozen spectrum analysis waveform of a Doppler shift frequency.

11. The ultrasonic diagnostic apparatus according to claim 5, wherein said imaging means outputs a Doppler flow mapped image, and wherein said recording/playback control means reproduces a frozen Doppler flow mapped image.

12. The ultrasonic diagnostic apparatus according to claim 5, wherein said imaging means outputs an M-mode image and a Doppler flow mapped image, and said display means freezes the M-mode image at a desired time period, and said recording/playback control means reproduces the Doppler flow mapped image corresponding to said desired time period.

13. The ultrasonic diagnostic apparatus according to claim 5, wherein said imaging means outputs a B-mode image and a spectrum analysis waveform of a Doppler shift frequency, said display means freezes the spectrum analysis waveform at a desired time period, and said recording/playback control means reproduces the B-mode image corresponding to said desired time period.

14. The ultrasonic diagnostic apparatus according to claim 5, wherein said imaging means outputs a spectrum analysis waveform of a Doppler shift frequency and a Doppler flow mapped image, said display means freezes the spectrum analysis waveform at a desired time period, and said recording/playback control means reproduces the Doppler flow mapped image corresponding to said desired time period.

* * * * *

UNITED STATES PATENT AND TRADEMARK OFFICE
CERTIFICATE OF CORRECTION

PATENT NO. : 5,090,413

DATED : February 25, 1992

INVENTOR(S) : Yoshihisa Yoshioka

It is certified that error appears in the above-identified patent and that said Letters Patent is hereby corrected as shown below:

Claim 1, column 7, line 15, after "subject" Delete "a".

Signed and Sealed this

Twenty-eighth Day of September, 1993

Attest:

BRUCE LEHMAN

Attesting Officer

Commissioner of Patents and Trademarks